(12) United States Patent
Matsuzaki

(10) Patent No.: US 9,375,003 B2
(45) Date of Patent: Jun. 28, 2016

(54) PLANT DISEASE CONTROL COMPOSITION AND ITS USE

(75) Inventor: Yuichi Matsuzaki, Toyonaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/643,959

(22) PCT Filed: Apr. 25, 2011

(86) PCT No.: PCT/JP2011/002416
§ 371 (c)(1),
(2), (4) Date: Nov. 20, 2012

(87) PCT Pub. No.: WO2011/135833
PCT Pub. Date: Nov. 3, 2011

(65) Prior Publication Data
US 2013/0065854 A1 Mar. 14, 2013

(30) Foreign Application Priority Data

Apr. 28, 2010 (JP) ................. 2010-104093

(51) Int. Cl.
*A61K 31/41* (2006.01)
*A01N 43/64* (2006.01)
*A01N 43/56* (2006.01)

(52) U.S. Cl.
CPC ...................... *A01N 43/56* (2013.01)

(58) Field of Classification Search
CPC ..... A01N 55/00; A01N 43/653; A01N 43/56; A01N 43/80; A01N 43/82
USPC ............ 514/266.23, 361, 359, 378, 380, 383, 514/384, 385, 396, 399, 400
See application file for complete search history.

(56) References Cited

U.S. PATENT DOCUMENTS

| | | | |
|---|---|---|---|
| 4,536,506 A | 8/1985 | Marcoux et al. | |
| 4,742,074 A | 5/1988 | Nishida et al. | |
| 5,093,347 A | 3/1992 | Graneto et al. | |
| 5,948,819 A | 9/1999 | Ohtsuka et al. | |
| 7,232,836 B2 | 6/2007 | Lahm et al. | |
| 7,612,100 B2 | 11/2009 | Koyanagi et al. | |
| 7,902,231 B2 | 3/2011 | Lahm et al. | |
| 7,994,201 B2 | 8/2011 | Koyanagi et al. | |
| 8,148,521 B2 | 4/2012 | Lahm et al. | |
| 8,158,802 B2 | 4/2012 | Lahm et al. | |
| 8,765,636 B2 * | 7/2014 | Dahmen et al. | 504/100 |
| 2002/0019541 A1 | 2/2002 | Eberle et al. | |
| 2004/0214828 A1 | 10/2004 | Selby | |
| 2005/0222051 A1 | 10/2005 | Andersch et al. | |
| 2007/0004921 A1 | 1/2007 | Dunkel et al. | |
| 2007/0244121 A1 | 10/2007 | Walter et al. | |
| 2007/0265267 A1 | 11/2007 | Walter et al. | |
| 2008/0070785 A1 | 3/2008 | Walter et al. | |
| 2009/0104145 A1 | 4/2009 | Hughes et al. | |
| 2009/0123561 A1 | 5/2009 | Gewehr et al. | |
| 2009/0181956 A1 | 7/2009 | Ikegami et al. | |
| 2009/0286681 A1 * | 11/2009 | Dahmen et al. | 504/100 |
| 2010/0048396 A1 | 2/2010 | Cavell et al. | |
| 2010/0099559 A1 | 4/2010 | Dietz et al. | |
| 2010/0120866 A1 | 5/2010 | Nokura et al. | |
| 2010/0216640 A1 | 8/2010 | Tobler et al. | |
| 2010/0248960 A1 | 9/2010 | Strathmann et al. | |
| 2011/0098176 A1 | 4/2011 | Gewehr et al. | |
| 2011/0105321 A1 | 5/2011 | Breuninger et al. | |
| 2011/0105579 A1 | 5/2011 | Wilhelm et al. | |
| 2011/0218100 A1 * | 9/2011 | Dahmen et al. | 504/100 |

(Continued)

FOREIGN PATENT DOCUMENTS

| | | |
|---|---|---|
| EA | 011551 B1 | 4/2009 |
| EA | 011585 B1 | 4/2009 |

(Continued)

OTHER PUBLICATIONS

International Search Report for International Patent Application No. PCT/JP2011/002416, dated May 31, 2011.
DELP, "Coping with Resistance to Plant Disease," Plant Disease, vol. 64, No. 7, Jul. 1980, pp. 652-657.
International Search Report for International Patent Application No. PCT/JP2011/002410, dated Jun. 28, 2011.
International Search Report for International Patent Application No. PCT/JP2011/002411, dated Jul. 5, 2011.
International Search Report for International Patent Application No. PCT/JP2011/002413, dated Jul. 19, 2011.
International Search Report for International Patent Application No. PCT/JP2011/002414, dated Jul. 12, 2011.

(Continued)

*Primary Examiner* — My-Chau T Tran
(74) *Attorney, Agent, or Firm* — Birch, Stewart, Kolasch & Birch, LLP

(57) ABSTRACT

A composition comprising a carboxamide compound represented by following formula (I), wherein $R^1$ represents a hydrogen atom or a methyl group, and $R^2$ represents a methyl group, a difluoromethyl group or a trifluoromethyl group, and one or more azole compounds selected from group (A) consisting of propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, ipconazole, simeconazole, hymexazol, etridiazole and flutriafol.

(I)

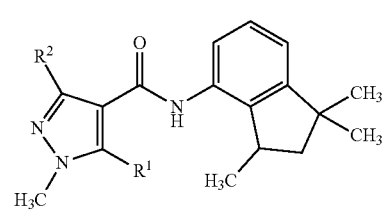

5 Claims, No Drawings

(56) References Cited

U.S. PATENT DOCUMENTS

| | | | |
|---|---|---|---|
| 2011/0257231 A1 | 10/2011 | Koyanagi et al. | |
| 2011/0319262 A1 | 12/2011 | Schade et al. | |
| 2012/0171183 A1 | 7/2012 | Lahm et al. | |
| 2013/0053424 A1* | 2/2013 | Matsuzaki | 514/406 |
| 2013/0059894 A1* | 3/2013 | Matsuzaki | 514/357 |
| 2014/0141972 A1 | 5/2014 | Berger et al. | |

FOREIGN PATENT DOCUMENTS

| | | |
|---|---|---|
| JP | 62-96472 A | 5/1987 |
| JP | 3729825 B2 | 12/2005 |
| JP | 2006-213665 A | 8/2006 |
| JP | 2007-182422 A | 7/2007 |
| JP | 2008-509189 A | 3/2008 |
| JP | 2008-515834 A | 5/2008 |
| JP | 4150379 B2 | 9/2008 |
| JP | 2008-280335 A | 11/2008 |
| JP | 2009-502747 A | 1/2009 |
| JP | 2010-13389 A | 1/2010 |
| JP | 2010-83869 A | 4/2010 |
| JP | 2010-83883 A | 4/2010 |
| RU | 2003 125 855 A | 1/2005 |
| RU | 2264388 C2 | 11/2005 |
| RU | 2 292 138 C2 | 1/2007 |
| RU | 2298007 C2 | 4/2007 |
| WO | WO 86/02641 A1 | 5/1986 |
| WO | WO 92/12970 A1 | 8/1992 |
| WO | WO 95/27693 A1 | 10/1995 |
| WO | WO 02/059086 A1 | 8/2002 |
| WO | WO 2004/067528 A1 | 8/2004 |
| WO | WO 2005/077934 A1 | 8/2005 |
| WO | WO 2007/095229 A2 | 8/2007 |
| WO | WO 2007/108483 A1 | 9/2007 |
| WO | WO 2008/046533 A2 | 4/2008 |
| WO | WO 2008/087163 A2 | 7/2008 |
| WO | WO 2008/113654 A2 | 9/2008 |
| WO | WO 2008/126933 A2 | 10/2008 |
| WO | WO 2008/131901 A1 | 11/2008 |
| WO | WO 2009/056620 A2 | 5/2009 |
| WO | WO 2009/062905 A1 | 5/2009 |
| WO | WO 2009/098223 A2 | 8/2009 |
| WO | WO 2009/119872 A2 | 10/2009 |
| WO | WO 2010/000790 A1 | 1/2010 |
| WO | WO 2010/021404 A2 | 2/2010 |
| WO | WO 2010/024365 A1 | 3/2010 |
| WO | WO 2010/024422 A1 | 3/2010 |
| WO | WO 2010/040623 A1 | 4/2010 |

OTHER PUBLICATIONS

International Search Report for International Patent Application No. PCT/JP2011/002415, dated Jul. 19, 2011.
International Search Report for International Patent Application No. PCT/JP2011/002417, dated Jul. 26, 2011.
International Search Report for International Patent Application No. PCT/JP2011/002418, dated May 31, 2011.
International Search Report for International Patent Application No. PCT/JP2011/002419, dated May 31, 2011.
International Search Report for International Patent Application No. PCT/JP2011/002420, dated May 31, 2011.
International Search Report for International Patent Application No. PCT/JP2011/002421, dated May 31, 2011.
International Search Report for International Patent Application No. PCT/JP2011/002422, dated May 31, 2011.
International Search Report for International Patent Application No. PCT/JP2011/002423, dated Jul. 19, 2011.
Office Action for U.S. Appl. No. 13/643,576, dated Jun. 12, 2013.
Office Action for U.S. Appl. No. 13/643,577, dated Jun. 11, 2013.
Office Action for U.S. Appl. No. 13/643,818, dated Aug. 20, 2013.
Office Action for U.S. Appl. No. 13/643,846, dated Aug. 7, 2013.
Office Action for U.S. Appl. No. 13/643,913, dated Apr. 26, 2013.
Office Action for U.S. Appl. No. 13/643,960, dated Aug. 1, 2013.
Extended European Search Report, dated Aug. 27, 2013, for Patent Application No. 11774619.8.
Russian Decision on Grant for Russian Application No. 2012150802/13, mailed Apr. 15, 2015, with an English translation.
Russian Decision on Grant for Russian Application No. 2012150829/13, mailed Apr. 10, 2015, with an English translation.
Japanese Office Action dated Jan. 13, 2015, for Japanese Application No. 2011-097979 with the English translation.
Japanese Office Action dated Jan. 27, 2015, for Japanese Application No. 2011-099111 with the English translation.
Japanese Office Action dated Jan. 27, 2015, for Japanese Application No. 2011-099112 with the English translation.
Japanese Office Action dated Jan. 6, 2015, for Japanese Application No. 2011-096842 with the English translation.
Japanese Office Action dated Jan. 6, 2015, for Japanese Application No. 2011-096843 with the English translation.
Japanese Office Action dated Jan. 6, 2015, for Japanese Application No. 2011-097978 with the English translation.
Chilean Office Action and Search Report, issued Apr. 24, 2015, in the corresponding Chilean Patent Application No. 2012-002988, along with an English translation of the Chilean Office Action.
Chilean Office Action and Search Report, issued May 15, 2015 for corresponding Chilean Patent Application No. 2012-002990.
Chilean Office Action and Search Report, issued May 22, 2015 for corresponding Chilean Patent Application No. 2012-002976, along with an English translation of the Chilean Office Action.
Oda et al., "Quantitative Structure-Activity Relationships of 2-Chloropyridine-3-carboxamide Fungicides," Journal of Pesticide Science, vol. 18, No. 1, Feb. 1993, XP009026800, pp. 49-57.
Chilean Application CL2011/00761, filed Apr. 6, 2011, along with an English abstract.
English translation of Chilean Office Action, issued May 15, 2015, for Chilean Application No. 2012-002990.
Russian Decision on Grant, issued Jul. 2, 2015, for Russian Application No. 2012150502, along with an English translation.
Russian Decision on Grant, issued Jun. 29, 2015, for Russian Application No. 2012150804, along with an English translation.
Russian Decision on Grant, issued May 29, 2015, for Russian Application No. 2012150436, along with an English translation.

* cited by examiner

PLANT DISEASE CONTROL COMPOSITION AND ITS USE

TECHNICAL FIELD

The present invention relates to a plant disease control composition and its use.

BACKGROUND ART

Many compounds have been developed for controlling plant disease and actually used (see, for example, PTL 1 and 2).

CITATION LIST

Patent Literature

[PTL 1]: WO86/02641
[PTL 2]: WO92/12970

SUMMARY OF INVENTION

Technical Problem

An object of the present invention is to provide a composition having an excellent effect for controlling plant disease.

Solution to Problem

The inventor of the present invention studied for seeking a composition having an excellent effect for plant disease and found that a composition comprising a carboxamide compound represented by the following formula (I) and one or more azole compounds selected from following group (A) has an excellent effect for controlling plant disease and then completed the present invention.

The present invention provides the following [1] to [5].

[1] A plant disease control composition comprising a carboxamide compound represented by formula (I):

[Chem. 1]

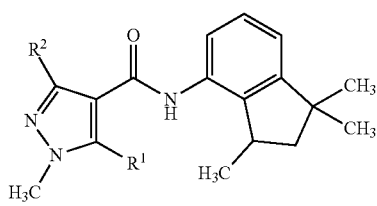

(I)

wherein
$R^1$ represents a hydrogen atom or a methyl group, and
$R^2$ represents a methyl group, a difluoromethyl group or a trifluoromethyl group,
and one or more azole compounds selected from group (A) consisting of propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, ipconazole, simeconazole, hymexazol, etridiazole and flutriafol.

[2] The plant disease control composition according to above [1], wherein the weight ratio of the carboxamide compound to azole compound(s) is from 0.1/1 to 10/1 of the carboxamide compound/the azole compound(s).

[3] A method of controlling plant disease which comprises a step of treating a plant or the soil where a plant grows with an effective amount of a carboxamide compound represented by formula (I):

[Chem. 2]

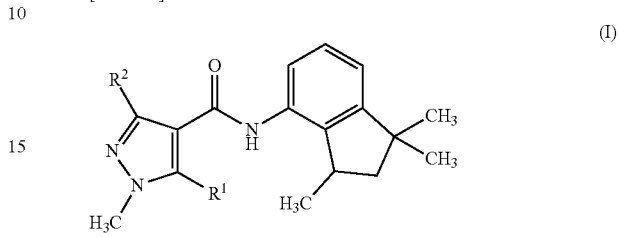

(I)

wherein
$R^1$ represents a hydrogen atom or a methyl group, and
$R^2$ represents a methyl group, a difluoromethyl group or a trifluoromethyl group, and one or more azole compounds selected from group (A) consisting of propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, ipconazole, simeconazole, hymexazol, etridiazole and flutriafol.

[4] The method of controlling plant disease according to above [3], wherein the weight ratio of the carboxamide compound to the azole compound(s) is from 0.1/1 to 10/1 of the carboxamide compound/the azole compound (s).

[5] The method of controlling plant disease according to above [3] or [4], wherein the plant or the soil where a plant grows is soybean or the soil where soybean grows, respectively.

Advantageous Effect of Invention

According to the present invention, various plant diseases can be controlled.

DESCRIPTION OF EMBODIMENTS

The plant disease control composition of the present invention (hereinafter referred to as "composition") comprises a carboxamide compound represented by formula (I):

[Chem. 3]

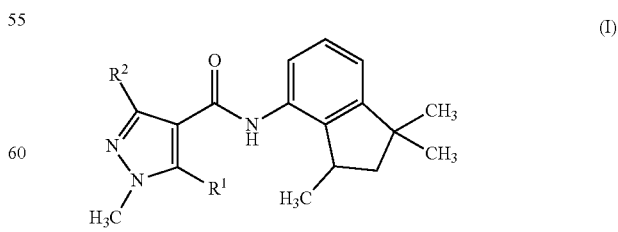

(I)

wherein
$R^1$ and $R^2$ represent the same meanings as defined in the above (hereinafter referred to as "carboxamide compound"), and one or more azole compounds selected from group (A) consisting of propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, ipconazole, simeconazole, hymexazol, etridiazole and flutriafol (hereinafter referred to as "azole compound").

The "carboxamide compounds" are those as described in, for example, WO86/02641or WO92/12970 and can be prepared by the method described therein.

Particular examples of the "carboxamide compounds" are as follows:
carboxamide compound represented by formula (1):

[Chem. 4]

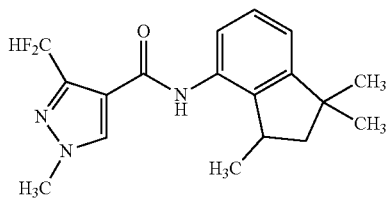

(1)

(hereinafter referred to as "carboxamide compound (1)");
carboxamide compound represented by formula (2):

[Chem. 5]

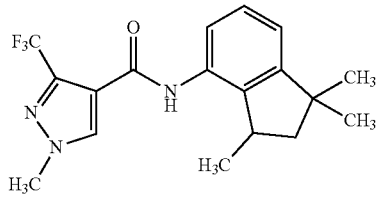

(2)

(hereinafter referred to as "carboxamide compound (2)");
carboxamide compound represented by formula (3):

[Chem. 6]

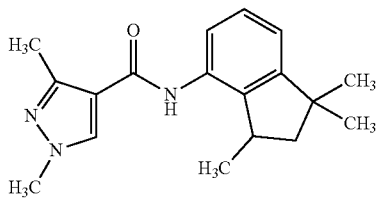

(3)

(hereinafter referred to as "carboxamide compound (3)"):
carboxamide compound represented by formula (4):

[Chem. 7]

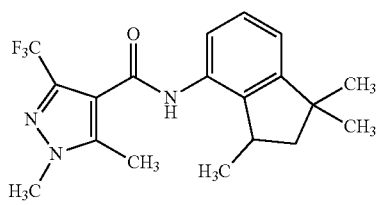

(4)

(hereinafter referred to as "carboxamide compound (4)";
carboxamide compound represented by formula (5):

[Chem. 8]

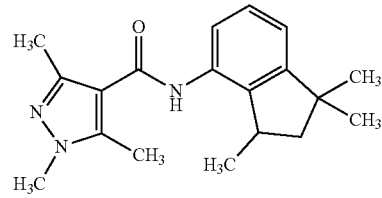

(5)

(hereinafter referred to as "carboxamide compound (5)").

The "azole compounds" are known compounds and described in, for example, "THE PESTICIDE MANUAL—14$^{th}$ EDITION (published by BCPC) ISBN 1901396142.

These compounds can be obtained from the products containing said "azole compound" in the market or can be synthesized by publicly known methods.

The weight ratio of the "carboxamide compound" to the "azole compound(s)" in the "composition" is usually from 0.01/1 to 500/1, and preferably from 0.1/1 to 10/1 of the carboxamide compound/the azole compound(s).

Although the "composition" may be a mixture itself of a "carboxamide compound" and "azole compound(s)", the "composition" is usually prepared by mixing a "carboxamide compound", "azole compound(s)" and an inert carrier, and if necessary, by adding a surfactant and/or another auxiliary for formulation and by formulating the mixture into oil formulation, emulsifiable concentrate, flowable formulation, wettable powder, water dispersible granules, powder, granules, or the like.

The formulation, which is used alone or by adding another inert component, can be used as a pesticide.

The total content of a "carboxamide compound" and "azole compound(s)" in a "composition" is usually from 0.1 to 99% by weight, preferably from 0.2 to 90% by weight, and more preferably from 1 to 80% by weight.

Examples of the solid carriers used for the formulation include fine powder or granules of, for example, mineral materials such as kaolin clay, attapulgite, bentonite, montmorillonite, acid clay, pyrophillite, talc, diatomaceous earth, and calcite; natural organic materials such as corncob powder, and walnut powder; synthetic organic materials such as urea; salts such as potassium carbonate, and ammonium sulfate; synthetic inorganic materials such as synthetic hydrous silicon oxide.

Examples of the liquid carriers include aromatic hydrocarbons such as xylene, alkylbenzene, and methylnaphthalene; alcohols such as 2-propanol, ethylene glycol, propylene glycol, and ethylene glycol mono-ethyl ether; ketones such as acetone, cyclohexanone, and isophorone; vegetable oils such as soybean oil, cotton seed oil; petrolic aliphatic hydrocarbons; esters; dimethylsulfoxide; acetonitrile; water.

Examples of the surfactants include anionic surfactants such as alkyl sulfate ester salts, alkylarylsulfonate salts, dialkylsulfosuccinate salts, polyoxyethylene alkylaryl ether phosphoric acid ester salts, lignin sulfonate, and naphthalene sulfonate formaldehyde poly condensed products; non-ionic surfactants such as polyoxyethylene alkyl aryl ethers, polyoxyethylene alkyl polyoxypropylene block copolymers, and sorbitan fatty acid esters; and cationic surfactants such as alkyl trimethyl ammonium salts.

Examples of the other auxiliaries for formulation include water-soluble polymers such as polyvinyl alcohol, and polyvinylpyrrolidone; polysaccharides such as gum arabic, alginic acid and its salt, CMC (carboxymethylcellulose), and xanthan gum; inorganic materials such as aluminum magnesium silicate, alumina sol; preservatives; coloring agents; and stabilizers such as PAP (acidic isopropyl phosphate), BHT.

The "composition" can be also prepared by formulating a "carboxamide compound" and "azole compound(s)" according to the method as described in the above, then mixing the formulations or their diluents.

The "composition" can be used for protecting a plant from plant disease.

Examples of plant diseases which can be controlled by the "composition" include the followings.

Rice diseases: *Magnaporthe grisea, Cochliobolus miyabeanus, Rhizoctonia solani, Gibberella fujikuroi;*

Wheat diseases: *Erysiphe graminis, Fusarium graminearum, F. avenaceum, F. culmorum, Microdochium nivale, Puccinia striiformis, P. graminis, P. recondita, Micronectriella nivale, Typhula* sp., *Ustilago tritici, Tilletia caries, Pseudocercosporella herpotrichoides, Mycosphaerella graminicola, Stagonospora nodorum, Pyrenophora tritici-repentis;*

Barley diseases: *Erysiphe graminis, Fusarium graminearum, F. avenaceum, F. culmorum, Microdochium nivale, Puccinia striiformis, P. graminis, P. hordei, Ustilago nuda, Pvhynchosporium secalis, Pyrenophora teres, Cochliobolus sativus, Pyrenophora graminea, Rhizoctonia solani;*

Maize diseases: *Ustilago maydis, Cochliobolus heterostrophus, Gloeocercospora sorghi, Puccinia polysora, Cercospora zeae-maydis, Rhizoctonia solani;*

Citrus diseases: *Diaporthe citri, Elsinoe fawcetti, Penicillium digitatum, P. italicum, Phytophthora parasitica, Phytophthora citrophthora;*

Apple diseases: *Monilinia mali, Valsa ceratosperma, Podosphaera leucotricha, Alternaria alternata apple pathotype, Venturia inaequalis, Colletotrichum acutatum, Phytophtora cactorum;*

Pear diseases: *Venturia nashicola, V. pirina, Alternaria alternata* Japanese pear pathotype, *Gymnosporangium haraeanum, Phytophtora cactorum;*

Peach diseases: *Monilinia fructicola, Cladosporium carpophilum, Phomopsis* sp.;

Grape diseases: *Elsinoe ampelina, Glomerella cingulata, Uninula necator, Phakopsora ampelopsidis, Guignardia bidwellii, Plasmopara viticola;*

Persimmon diseases: *Gloesporium kaki, Cercospora kaki, Mycosphaerela nawae;*

Gourd diseases: *Colletotrichum lagenarium, Sphaerotheca fuliginea, Mycosphaerella melonis, Fusarium oxysporum, Pseudoperonospora cubensis, Phytophthora* sp., *Pythium* sp.;

Tomato diseases: *Alternaria solani, Cladosporium fulvum, Phytophthora infestans;*

Eggplant diseases: *Phomopsis vexans, Erysiphe cichoracearum;*

Brassicaceous vegetable diseases: *Alternaria japonica, Cercosporella brassicae, Plasmodiophora brassicae, Peronospora parasitica;*

Welsh onion diseases: *Puccinia allii, Peronospora destructor;*

Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani, Corynespora casiicola, Sclerotinia sclerotiorum;*

Kidney bean diseases: *Colletrichum lindemthianum;*

Peanut diseases: *Cercospora personata, Cercospora arachidicola, Sclerotium rolfsii;*

Pea diseases pea: *Erysiphe pisi;*

Potato diseases: *Alternaria solani, Phytophthora infestans, Phytophthora erythroseptica, Spongospora subterranean,* f. sp. *Subterranean;*

Strawberry diseases: *Sphaerotheca humuli, Glomerella cingulata;*

Tea diseases: *Exobasidium reticulatum, Elsinoe leucospila, Pestalotiopsis* sp., *Colletotrichum theae-sinensis;*

Tobacco diseases: *Alternaria longipes, Erysiphe cichoracearum, Colletotrichum tabacum, Peronospora tabacina, Phytophthora nicotianae;*

Rapeseed diseases: *Sclerotinia sclerotiorum, Rhizoctonia solani;*

Cotton diseases: *Rhizoctonia solani;*

Beet diseases: *Cercospora beticola, Thanatephorus cucumeris, Thanatephorus cucumeris, Aphanomyces cochlioides;*

Rose diseases: *Diplocarpon rosae, Sphaerotheca pannosa, Peronospora sparsa;*

Diseases of chrysanthemum and asteraceae: *Bremia lactuca, Septoria chrysanthemiindici, Puccinia horiana;*

Diseases of various plants: *Pythium aphanidermatum, Pythium debarianum, Pythium graminicola, Pythium irregulare, Pythium ultimum, Botrytis cinerea, Sclerotinia sclerotiorum;*

Radish diseases: *Alternaria brassicicola;*

Zoysia diseases: *Sclerotinia homeocarpa, Rhizoctonia solani;*

Banana diseases: *Mycosphaerella fijiensis, Mycosphaerella musicola;*

Sunflower diseases: *Plasmopara halstedii;*

Seed diseases or diseases in the initial stage of growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Rhoma* spp., *Rhizoctonia* spp., *Diplodia* spp., or the like;

Virus diseases of various plants mediated by *Polymixa* spp., *Olpidium* spp., or the like.

Examples of the plants for which the "composition" can be used are as follows

Agricultural crops: maize, rice, wheat, barley, rye, oat, sorghum, cotton, soybean, peanut, buckwheat, sugar beet, rapeseed, sunflower, sugar cane, tobacco plant, and the like;

Vegetables: Solanaceous vegetables (eggplant, tomato, green pepper, hot pepper, potato, etc.), Cucurbitaceous vegetables (cucumber, pumpkin, zucchini, watermelon, melon, squash, etc.); Cruciferous vegetables (radish, turnip, horseradish, kohlrabi, Chinese cabbage, cabbage, brown mustard, broccoli, cauliflower, etc.), Asteraceous vegetables (burdock, garland chrysanthemum, artichoke, lettuce, etc.), Liliaceous vegetables (Welsh onion, onion, garlic, asparagus, etc.), Umbelliferous vegetables (carrot, parsley, celery, parsnip, etc.), Chenopodiaceous vegetables (spinach, chard, etc.), Lamiaceous vegetables (Japanese basil, mint, basil, etc.), strawberry, sweet potato, yam, aroid, and the like;

Flowering plants;

Ornamental foliage plants;

Turf;

Fruit trees: pome fruits (apple, common pear, Japanese pear, Chinese quince, quince, etc.), stone fruits (peach, plum, nectarine, Japanese plum, cherry, apricot, prune, etc.), citrus (mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut palm, and the like;

Trees other than fruit trees: tea, mulberry, flowering trees, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew), and the like.

The above-described plants may be those having resistance imparted by genetic engineering technique.

Among the above plants, the "composition" is expected to have excellent controlling effect particularly to plant diseases caused in soybean.

Among the above plant diseases, the soybean diseases to which especially excellent effect of the "composition" can be expected are *Rhizoctonia solani, Cercospora kikuchii, Septoria glycines, Corynespora casiicola, Phakopsora pachyrizi, Sclerotinia sclerotiorum, Cercospora sojina*, and the like.

Following compositions exemplify an embodiment of the "composition":

a composition comprising "carboxamide compound (1)" and propiconazole;
a composition comprising "carboxamide compound (1)" and prothioconazole;
a composition comprising "carboxamide compound (1)" and triadimenol;
a composition comprising "carboxamide compound (1)" and prochloraz;
a composition comprising "carboxamide compound (1)" and tebuconazole;
a composition comprising "carboxamide compound (1)" and flusilazole;
a composition comprising "carboxamide compound (1)" and diniconazole;
a composition comprising "carboxamide compound (1)" and bromuconazole;
a composition comprising "carboxamide compound (1)" and epoxiconazole;
a composition comprising "carboxamide compound (1)" and difenoconazole;
a composition comprising "carboxamide compound (1)" and cyproconazole;
a composition comprising "carboxamide compound (1)" and metconazole;
a composition comprising "carboxamide compound (1)" and tetraconazole;
a composition comprising "carboxamide compound (1)" and fluquinconazole;
a composition comprising "carboxamide compound (1)" and triticonazole;
a composition comprising "carboxamide compound (1)" and ipconazole;
a composition comprising "carboxamide compound (2)" and propiconazole;
a composition comprising "carboxamide compound (2)" and prothioconazole;
a composition comprising "carboxamide compound (2)" and triadimenol;
a composition comprising "carboxamide compound (2)" and prochloraz;
composition comprising "carboxamide compound (2)" and tebuconazole;
a composition comprising "carboxamide compound (2)" and flusilazole;
a composition comprising "carboxamide compound (2)" and diniconazole;
a composition comprising "carboxamide compound (2)" and bromuconazole;
a composition comprising "carboxamide compound (2)" and epoxiconazole;
a composition comprising "carboxamide compound (2)" and difenoconazole;
a composition comprising "carboxamide compound (2)" and cyproconazole;
a composition comprising "carboxamide compound (2)" and metconazole;
a composition comprising "carboxamide compound (2)" and tetraconazole;
a composition comprising "carboxamide compound (2)" and fluquinconazole;
a composition comprising "carboxamide compound (2)" and triticonazole;
a composition comprising "carboxamide compound (2)" and ipconazole;
a composition comprising "carboxamide compound (3)" and propiconazole;
a composition comprising "carboxamide compound (3)" and prothioconazole;
a composition comprising "carboxamide compound (3)" and triadimenol;
a composition comprising "carboxamide compound (3)" and prochloraz;
a composition comprising "carboxamide compound (3)" and tebuconazole;
a composition comprising "carboxamide compound (3)" and flusilazole;
a composition comprising "carboxamide compound (3)" and diniconazole;
a composition comprising "carboxamide compound (3)" and bromuconazole;
a composition comprising "carboxamide compound (3)" and epoxiconazole;
a composition comprising "carboxamide compound (3)" and difenoconazole;
a composition comprising "carboxamide compound (3)" and cyproconazole;
a composition comprising "carboxamide compound (3)" and metconazole;
a composition comprising "carboxamide compound (3)" and tetraconazole;
a composition comprising "carboxamide compound (3)" and fluquinconazole;
a composition comprising "carboxamide compound (3)" and triticonazole;
a composition comprising "carboxamide compound (3)" and ipconazole;
a composition comprising "carboxamide compound (4)" and propiconazole;
a composition comprising "carboxamide compound (4)" and prothioconazole;
a composition comprising "carboxamide compound (4)" and triadimenol;
a composition comprising "carboxamide compound (4)" and prochloraz;
a composition comprising "carboxamide compound (4)" and tebuconazole;
a composition comprising "carboxamide compound (4)" and flusilazole;
a composition comprising "carboxamide compound (4)" and diniconazole;
a composition comprising "carboxamide compound (4)" and bromuconazole;
a composition comprising "carboxamide compound (4)" and epoxiconazole;

a composition comprising "carboxamide compound (4)" and difenoconazole;
a composition comprising "carboxamide compound (4)" and cyproconazole;
a composition comprising "carboxamide compound (4)" and metconazole;
a composition comprising "carboxamide compound (4)" and tetraconazole;
a composition comprising "carboxamide compound (4)" and fluquinconazole;
a composition comprising "carboxamide compound (4)" and triticonazole;
a composition comprising "carboxamide compound (4)" and ipconazole;
a composition comprising "carboxamide compound (5)" and propiconazole;
a composition comprising "carboxamide compound (5)" and prothioconazole;
a composition comprising "carboxamide compound (5)" and triadimenol;
a composition comprising "carboxamide compound (5)" and prochloraz;
a composition comprising "carboxamide compound (5)" and tebuconazole;
a composition comprising "carboxamide compound (5)" and flusilazole;
a composition comprising "carboxamide compound (5)" and diniconazole;
a composition comprising "carboxamide compound (5)" and bromuconazole;
a composition comprising "carboxamide compound (5)" and epoxiconazole;
a composition comprising "carboxamide compound (5)" and difenoconazole;
a composition comprising "carboxamide compound (5)" and cyproconazole;
a composition comprising "carboxamide compound (5)" and metconazole;
a composition comprising "carboxamide compound (5)" and tetraconazole;
a composition comprising "carboxamide compound (5)" and fluquinconazole;
a composition comprising "carboxamide compound (5)" and triticonazole;
a composition comprising "carboxamide compound (5)" and ipconazole;
a composition comprising "carboxamide compound (1)" and propiconazole in which the weight ratio of "carboxamide compound (1)" to propiconazole is 0.1/1 to 10/1;
a composition comprising "carboxamide compound (1)" and prothioconazole in which the weight ratio of "carboxamide compound (1)" to prothioconazole is 0.1/1 to 10/1;
a composition comprising "carboxamide compound (1)" and triadimenol in which the weight ratio of "carboxamide compound (1)" to triadimenol is 0.1/1 to 10/1;
a composition comprising "carboxamide compound (1)" and prochloraz in which the weight ratio of "carboxamide compound (1)" to prochloraz is 0.1/1 to 10/1;
a composition comprising "carboxamide compound (1)" and tebuconazole in which the weight ratio of "carboxamide compound (1)" to tebuconazole is 0.1/1 to 10/1;
a composition comprising "carboxamide compound (1)" and flusilazole in which the weight ratio of "carboxamide compound (1)" to flusilazole is 0.1/1 to 10/1;
a composition comprising "carboxamide compound (1)" and diniconazole in which the weight ratio of "carboxamide compound (1)" to diniconazole is 0.1/1 to 10/1;
a composition comprising "carboxamide compound (1)" and bromuconazole in which the weight ratio of "carboxamide compound (1)" to bromuconazole is 0.1/1 to 10/1;
a composition comprising "carboxamide compound (1)" and epoxiconazole in which the weight ratio of "carboxamide compound (1)" to epoxiconazole is 0.1/1 to 10/1;
a composition comprising "carboxamide compound (1)" and difenoconazole in which the weight ratio of "carboxamide compound (1)" to difenoconazole is 0.1/1 to 10/1;
a composition comprising "carboxamide compound (1)" and cyproconazole in which the weight ratio of "carboxamide compound (1)" to cyproconazole is 0.1/1 to 10/1;
a composition comprising "carboxamide compound (1)" and metconazole in which the weight ratio of "carboxamide compound (1)" to metconazole is 0.1/1 to 10/1;
a composition comprising "carboxamide compound (1)" and tetraconazole in which the weight ratio of "carboxamide compound (1)" to tetraconazole is 0.1/1 to 10/1;
a composition comprising "carboxamide compound (1)" and fluquinconazole in which the weight ratio of "carboxamide compound (1)" to fluquinconazole is 0.1/1 to 10/1;
a composition comprising "carboxamide compound (1)" and triticonazole in which the weight ratio of "carboxamide compound (1)" to triticonazole is 0.1/1 to 10/1;
a composition comprising "carboxamide compound (1)" and ipconazole in which the weight ratio of "carboxamide compound (1)" to ipconazole is 0.1/1 to 10/1;
a composition comprising "carboxamide compound (2)" and propiconazole in which the weight ratio of "carboxamide compound (2)" to propiconazole is 0.1/1 to 10/1;
a composition comprising "carboxamide compound (2)" and prothioconazole in which the weight ratio of "carboxamide compound (2)" to prothioconazole is 0.1/1 to 10/1;
a composition comprising "carboxamide compound (2)" and triadimenol in which the weight ratio of "carboxamide compound (2)" to triadimenol is 0.1/1 to 10/1;
a composition comprising "carboxamide compound (2)" and prochloraz in which the weight ratio of "carboxamide compound (2)" to prochloraz is 0.1/1 to 10/1;
a composition comprising "carboxamide compound (2)" and tebuconazole in which the weight ratio of "carboxamide compound (2)" to tebuconazole is 0.1/1 to 10/1;
a composition comprising "carboxamide compound (2)" and flusilazole in which the weight ratio of "carboxamide compound (2)" to flusilazole is 0.1/1 to 10/1;
a composition comprising "carboxamide compound (2)" and diniconazole in which the weight ratio of "carboxamide compound (2)" to diniconazole is 0.1/1 to 10/1;
a composition comprising "carboxamide compound (2)" and bromuconazole in which the weight ratio of "carboxamide compound (2)" to bromuconazole is 0.1/1 to 10/1;
a composition comprising "carboxamide compound (2)" and epoxiconazole in which the weight ratio of "carboxamide compound (2)" to epoxiconazole is 0.1/1 to 10/1;
a composition comprising "carboxamide compound (2)" and difenoconazole in which the weight ratio of "carboxamide compound (2)" to difenoconazole is 0.1/1 to 10/1;
a composition comprising "carboxamide compound (2)" and cyproconazole in which the weight ratio of "carboxamide compound (2)" to cyproconazole is 0.1/1 to 10/1;
a composition comprising "carboxamide compound (2)" and metconazole in which the weight ratio of "carboxamide compound (2)" to metconazole is 0.1/1 to 10/1;
a composition comprising "carboxamide compound (2)" and tetraconazole in which the weight ratio of "carboxamide compound (2)" to tetraconazole is 0.1/1 to 10/1;

a composition comprising "carboxamide compound (2)" and fluquinconazole in which the weight ratio of "carboxamide compound (2)" to/fluquinconazole is 0.1/1 to 10/1;

a composition comprising "carboxamide compound (2)" and triticonazole in which the weight ratio of "carboxamide compound (2)" to triticonazole is 0.1/1 to 10/1;

a composition comprising "carboxamide compound (2)" and ipconazole in which the weight ratio of "carboxamide compound (2)" to ipconazole is 0.1/1 to 10/1;

a composition comprising "carboxamide compound (3)" and propiconazole in which the weight ratio of "carboxamide compound (3)" to propiconazole is 0.1/1 to 10/1;

a composition comprising "carboxamide compound (3)" and prothioconazole in weight ratio of "carboxamide compound (3)" to prothioconazole is 0.1/1 to 10/1;

a composition comprising "carboxamide compound (3)" and triadimenol in which the weight ratio of "carboxamide compound (3)" to triadimenol is 0.1/1 to 10/1;

a composition comprising "carboxamide compound (3)" and prochloraz in which the weight ratio of "carboxamide compound (3)" to prochloraz is 0.1/1 to 10/1;

a composition comprising "carboxamide compound (3)" and tebuconazole in which the weight ratio of "carboxamide compound (3)" to tebuconazole is 0.1/1 to 10/1;

a composition comprising "carboxamide compound (3)" and flusilazole in which the weight ratio of "carboxamide compound (3)" to flusilazole is 0.1/1 to 10/1;

a composition comprising "carboxamide compound (3)" and diniconazole in weight ratio of "carboxamide compound (3)" to diniconazole is 0.1/1 to 10/1;

a composition comprising "carboxamide compound (3)" and bromuconazole in which the weight ratio of "carboxamide compound (3)" to bromuconazole is 0.1/1 to 10/1;

a composition comprising "carboxamide compound (3)" and epoxiconazole in which the weight ratio of "carboxamide compound (3)" to epoxiconazole is 0.1/1 to 10/1;

a composition comprising "carboxamide compound (3)" and difenoconazole in which the weight ratio of "carboxamide compound (3)" to difenoconazole is 0.1/1 to 10/1;

a composition comprising "carboxamide compound (3)" and cyproconazole in which the weight ratio of "carboxamide compound (3)" to cyproconazole is 0.1/1 to 10/1;

a composition comprising "carboxamide compound (3)" and metconazole in which the weight ratio of "carboxamide compound (3)" to metconazole is 0.1/1 to 10/1;

a composition comprising "carboxamide compound (3)" and tetraconazole in which the weight ratio of "carboxamide compound (3)" to tetraconazole is 0.1/1 to 10/1;

a composition comprising "carboxamide compound (3)" and fluquinconazole in weight ratio of "carboxamide compound (3)" to fluquinconazole is 0.1/1 to 10/1;

a composition comprising "carboxamide compound (3)" and triticonazole in which the weight ratio of "carboxamide compound (3)" to triticonazole is 0.1/1 to 10/1;

a composition comprising "carboxamide compound (3)" and ipconazole in which the weight ratio of "carboxamide compound (3)" to ipconazole is 0.1/1 to 10/1;

a composition comprising "carboxamide compound (4)" and propiconazole in which the weight ratio of "carboxamide compound (4)" to propiconazole is 0.1/1 to 10/1;

a composition comprising "carboxamide compound (4)" and prothioconazole in which the weight ratio of "carboxamide compound (4)" to prothioconazole is 0.1/1 to 10/1;

a composition comprising "carboxamide compound (4)" and triadimenol in which the weight ratio of "carboxamide compound (4)" to triadimenol is 0.1/1 to 10/1;

a composition comprising "carboxamide compound (4)" and prochloraz in which the weight ratio of "carboxamide compound (4)" to prochloraz is 0.1/1 to 10/1;

a composition comprising "carboxamide compound (4)" and tebuconazole in which the weight ratio of "carboxamide compound (4)" to tebuconazole is 0.1/1 to 10/1;

a composition comprising "carboxamide compound (4)" and flusilazole in which the weight ratio of "carboxamide compound (4)" to flusilazole is 0.1/1 to 10/1;

a composition comprising "carboxamide compound (4)" and diniconazole in which the weight ratio of "carboxamide compound (4)" to diniconazole is 0.1/1 to 10/1;

a composition comprising "carboxamide compound (4)" and bromuconazole in which the weight ratio of "carboxamide compound (4)" to bromuconazole is 0.1/1 to 10/1;

a composition comprising "carboxamide compound (4)" and epoxiconazole in which the weight ratio of "carboxamide compound (4)" to epoxiconazole is 0.1/1 to 10/1;

a composition comprising "carboxamide compound (4)" and difenoconazole in which the weight ratio of "carboxamide compound (4)" to difenoconazole is 0.1/1 to 10/1;

a composition comprising "carboxamide compound (4)" and cyproconazole in which the weight ratio of "carboxamide compound (4)" to cyproconazole is 0.1/1 to 10/1;

a composition comprising "carboxamide compound (4)" and metconazole in which the weight ratio of "carboxamide compound (4)" to metconazole is 0.1/1 to 10/1;

a composition comprising "carboxamide compound (4)" and tetraconazole in which the weight ratio of "carboxamide compound (4)" to tetraconazole is 0.1/1 to 10/1;

a composition comprising "carboxamide compound (4)" and fluquinconazole in which the weight ratio of "carboxamide compound (4)" to fluquinconazole is 0.1/1 to 10/1;

a composition comprising "carboxamide compound (4)" and triticonazole in which the weight ratio of "carboxamide compound (4)" to triticonazole is 0.1/1 to 10/1;

a composition comprising "carboxamide compound (4)" and ipconazole in which the weight ratio of "carboxamide compound (4)" to ipconazole is 0.1/1 to 10/1;

a composition comprising "carboxamide compound (5)" and propiconazole in which the weight ratio of "carboxamide compound (5)" to propiconazole is 0.1/1 to 10/1;

a composition comprising "carboxamide compound (5)" and prothioconazole in which the weight ratio of "carboxamide compound (5)" to prothioconazole is 0.1/1 to 10/1;

a composition comprising "carboxamide compound (5)" and triadimenol in which the weight ratio of "carboxamide compound (5)" to triadimenol is 0.1/1 to 10/1;

a composition comprising "carboxamide compound (5)" and prochloraz in which the weight ratio of "carboxamide compound (5)" to prochloraz is 0.1/1 to 10/1;

a composition comprising "carboxamide compound (5)" and tebuconazole in which the weight ratio of "carboxamide compound (5)" to tebuconazole is 0.1/1 to 10/1;

a composition comprising "carboxamide compound (5)" and flusilazole in which the weight ratio of "carboxamide compound (5)" to flusilazole is 0.1/1 to 10/1;

a composition comprising "carboxamide compound (5)" and diniconazole in which the weight ratio of "carboxamide compound (5)" to diniconazole is 0.1/1 to 10/1;

a composition comprising "carboxamide compound (5)" and bromuconazole in which the weight ratio of "carboxamide compound (5)" to bromuconazole is 0.1/1 to 10/1;

a composition comprising "carboxamide compound (5)" and epoxiconazole in which the weight ratio of "carboxamide compound (5)" to epoxiconazole is 0.1/1 to 10/1;

a composition comprising "carboxamide compound (5)" and difenoconazole in which the weight ratio of "carboxamide compound (5)" to difenoconazole is 0.1/1 to 10/1;

a composition comprising "carboxamide compound (5)" and cyproconazole in which the weight ratio of "carboxamide compound (5)" to cyproconazole is 0.1/1 to 10/1;

a composition comprising "carboxamide compound (5)" and metconazole in which the weight ratio of "carboxamide compound (5)" to metconazole is 0.1/1 to 10/1;

a composition comprising "carboxamide compound (5)" and tetraconazole in which the weight ratio of "carboxamide compound (5)" to tetraconazole is 0.1/1 to 10/1;

a composition comprising "carboxamide compound (5)" and fluquinconazole in which the weight ratio of "carboxamide compound (5)" to fluquinconazole is 0.1/1 to 10/1;

a composition comprising "carboxamide compound (5)" and triticonazole in which the weight ratio of "carboxamide compound (5)" to triticonazole is 0.1/1 to 10/1;

a composition comprising "carboxamide compound (5)" and ipconazole in which the weight ratio of "carboxamide compound (5)" to ipconazole is 0.1/1 to 10/1.

The method of controlling plant disease (hereinafter referred to as "controlling method") can be carried out by treating a plant or the soil where a plant grows with an effective amount of a "carboxamide compound" and "azole compound(s)".

The part of plant to be treated is stem and leaf of a plant, seed or bulb of a plant, and the bulb means bulb, corm, rootstock, tuber, tuberous root and rhizophore.

In the "controlling method", the treatment of a plant or the soil where a plant grows with a "carboxamide compound" and "azole compound(s)" can be carried out separately at the same timing, but the treatment is usually carried out by using a "composition" in light of convenience.

In the "controlling method", the treatment with a carboxamide compound" and "azole compound(s)" is, for example, stems and leaves application, soil application, roots application or seeds application.

Examples of the stems and leaves application include a treatment for surface of cultivated plant by a stem and leave spray or a stem and tree.

Examples of the root application include a method of dipping a whole plant or root of a plant into a liquid containing a "carboxamide compound" and "azole compound(s)" and a method of sticking a solid preparation comprising a "carboxamide compound", "azole compound(s)" and a solid carrier onto root of a plant.

Examples of the soil application include a method of spraying a "composition" onto a soil, a method of mixing a "composition" with a soil and a method of irrigating a "composition" into the soil.

Examples of the seed application include a method of treating seeds or bulbs of a plant to be protected from a plant disease with a "composition". Particularly, the application can be carried out by spraying a suspension of a "composition" to the surface of seeds or bulbs, or by spreading wettable powder, emulsifiable concentrate or flowable formulation itself or a mixture thereof with a small amount of water on the seeds or the bulbs, or by dipping the seeds into a solution of a "composition" for a prescribed time, by film coating application or pellet coating application.

The amount of a "carboxamide compound" and "azole compound(s)" used in the "controlling method" is different depending on the kind of a plant to be treated, the kind of a plant disease to be controlled and its frequency, the kind of a formulation, timing of treatment, method of treatment, place of treatment, weather condition, and the like.

When a "composition" is applied to stems and/or leaves of a plant or to the soil where a plant grows, the total amount of a "carboxamide compound" and "azole compound(s)" is usually from 1 g to 500 g/1000 m$^2$, preferably from 2 g to 200 g/1000 m$^2$ and more preferably from 10 g to 100 g/1000 m$^2$.

When a "composition" is applied to seeds of a plant, the total amount of a "carboxamide compound" and "azole compound(s)" is usually from 0.001 g to 10 g/1 kg of the seeds, and preferably from 0.01 g to 1 g/1 kg of the seeds.

An emulsifiable concentrate, wettable powder or flowable formulation is usually by diluting the formulation with water and spraying the diluted formulation. In this case, the concentration of a "carboxamide compound" and "azole compound(s)" in total of the diluted formulation is usually from 0.0005 to 2% by weight and preferably from 0.005 to 1% by weight.

The powder formulation, granule formulation, and the like can be usually used without dilution.

EXAMPLE

The present invention is further explained in detail with Formulation Examples and Test Examples. However, the present invention is not limited by the following Examples.

In the following Examples, "part" means "part by weight" unless otherwise provided.

Formulation Example 1

One of "carboxamide compound" (1) to (5) (2.5 parts), propiconazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 2

One of "carboxamide compound" (1) to (5) (2.5 parts), prothioconazole (1.25 parts), poly oxy ethylene styryl phenyl ether (14 parts), calcium dodecylbenzene sulfonate (6 parts) and xylene (76.25 parts) are mixed well to give each of formulations, respectively.

Formulation Example 3

One of "carboxamide compound" (1) to (5) (2.5 parts), triadimenol (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 4

One of "carboxamide compound" (1) to (5) (2.5 parts), prochloraz (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 5

One of "carboxamide compound" (1) to (5) (2.5 parts), tebuconazole (1.25 parts), poly oxy ethylene styryl phenyl ether (14 parts), calcium dodecylbenzene sulfonate (6 parts) and xylene (76.25 parts) are mixed well to give each of formulations, respectively.

Formulation Example 6

One of "carboxamide compound" (1) to (5) (2.5 parts), flusilazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 7

One of "carboxamide compound" (1) to (5) (2.5 parts), diniconazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 8

One of "carboxamide compound" (1) to (5) (2.5 parts), bromuconazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 9

One of "carboxamide compound" (1) to (5) (2.5 parts), epoxiconazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 10

One of "carboxamide compound" (1) to (5) (2.5 parts), difenoconazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 11

One of "carboxamide compound" (1) to (5) (2.5 parts), cyproconazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 12

One of "carboxamide compound" (1) to (5) (2.5 parts), metconazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 13

One of "carboxamide compound" (1) to (5) (2.5 parts), tetraconazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 14

One of "carboxamide compound" (1) to (5) (2.5 parts), fluquinconazole (1.25 parts), poly oxy ethylene styryl phenyl ether (14 parts), calcium dodecylbenzene sulfonate (6 parts) and xylene (76.25 parts) are mixed well to give each of formulations, respectively.

Formulation Example 15

One of "carboxamide compound" (1) to (5) (2.5 parts), myclobutanil (1.25 parts), poly oxy ethylene styryl phenyl ether (14 parts), calcium dodecylbenzene sulfonate (6 parts) and xylene (76.25 parts) are mixed well to give each of formulations, respectively.

Formulation Example 16

One of "carboxamide compound" (1) to (5) (2.5 parts), ipconazole (1.25 parts), polyoxyethylene styryl phenyl ether (14 parts), calcium dodecylbenzene sulfonate (6 parts) and xylene (76.25 parts) are mixed well to give each of formulations, respectively.

Formulation Example 17

One of "carboxamide compound" (1) to (5) (2 parts), propiconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 18

One of "carboxamide compound" (1) to (5) (2 parts), prothioconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 19

One of "carboxamide compound" (1) to (5) (2 parts), triadimenol (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 20

One of "carboxamide compound" (1) to (5) (2 parts), hymexazol (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 21

One of "carboxamide compound" (1) to (5) (2 parts), tebuconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 22

One of "carboxamide compound" (1) to (5) (2 parts), flusilazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 23

One of "carboxamide compound" (1) to (5) (2 parts), diniconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 24

One of "carboxamide compound" (1) to (5) (2 parts), bromuconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 25

One of "carboxamide compound" (1) to (5) (2 parts), epoxiconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 26

One of "carboxamide compound" (1) to (5) (2 parts), difenoconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 27

One of "carboxamide compound" (1) to (5) (2 parts), cyproconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 28

One of "carboxamide compound" (1) to (5) (2 parts), metconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 29

One of "carboxamide compound" (1) to (5) (2 parts), tetraconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 30

One of "carboxamide compound" (1) to (5) (2 parts), fluquinconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 31

One of "carboxamide compound" (1) to (5) (2 parts), triticonazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 32

One of "carboxamide compound" (1) to (5) (2 parts), ipconazole (8 parts), a mixture of white carbon and polyoxyethylene alkyl ether sulfate ammonium salt (weight ratio 1:1) (35 parts) and water (55 parts) are mixed and the mixture is milled by wet-milling method to give each of formulations, respectively.

Formulation Example 33

One of "carboxamide compound" (1) to (5) (5 parts), propiconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 34

One of "carboxamide compounds" (1) to (5) (5 parts), prothioconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 35

One of "carboxamide compounds" (1) to (5) (5 parts), triadimenol (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 36

One of "carboxamide compounds" (1) to (5) (5 parts), prochloraz (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 37

One of "carboxamide compounds" (1) to (5) (5 parts), tebuconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 38

One of "carboxamide compounds" (1) to (5) (5 parts), flusilazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 39

One of "carboxamide compounds" (1) to (5) (5 parts), diniconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 40

One of "carboxamide compounds" (1) to (5) (5 parts), bromuconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 41

One of "carboxamide compounds" (1) to (5) (5 parts), epoxiconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 42

One of "carboxamide compounds" (1) to (5) (5 parts), difenoconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 43

One of "carboxamide compounds" (1) to (5) (5 parts), cyproconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 44

One of "carboxamide compounds" (1) to (5) (5 parts), metconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 45

One of "carboxamide compounds" (1) to (5) (5 parts), tetraconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 46

One of "carboxamide compounds" (1) to (5) (5 parts), fluquinconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 47

One of "carboxamide compounds" (1) to (5) (5 parts), triticonazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 48

One of "carboxamide compounds" (1) to (5) (5 parts), ipconazole (10 parts), sorbitan tri-oleate (1.5 parts) and an aqueous solution (28.5 parts) containing polyvinyl alcohol (2 parts) are mixed and the mixture is milled by wet-milling method. To the milled mixture is added an aqueous solution (45 parts) containing xanthan gum (0.05 parts) and aluminium magnesium silicate (0.1 part), and further propylene glycol (10 parts) is added to the mixture. The resultant mixture is mixed by stirring to give each of formulations, respectively.

Formulation Example 49

One of "carboxamide compounds" (1) to (5) (1 part), propiconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 50

One of "carboxamide compounds" (1) to (5) (1 part), prothioconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 51

One of "carboxamide compounds" (1) to (5) (1 part), triadimenol (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 52

One of "carboxamide compounds" (1) to (5) (1 part), prochloraz (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 53

One of "carboxamide compounds" (1) to (5) (1 part), tebuconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 54

One of "carboxamide compounds" (1) to (5) (1 part), flusilazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 55

One of "carboxamide compounds" (1) to (5) (1 part), diniconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 56

One of "carboxamide compounds" (1) to (5) (1 part), bromuconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 57

One of "carboxamide compounds" (1) to (5) (1 part), epoxiconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 58

One of "carboxamide compounds" (1) to (5) (1 part), difenoconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 59

One of "carboxamide compounds" (1) to (5) (1 part), cyproconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 60

One of "carboxamide compounds" (1) to (5) (1 part), metconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 61

One of "carboxamide compounds" (1) to (5) (1 part), tetraconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 62

One of "carboxamide compounds" (1) to (5) (1 part), fluquinconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 63

One of "carboxamide compounds" (1) to (5) (1 part), triflumizole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 64

One of "carboxamide compounds" (1) to (5) (1 part), ipconazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 65

One of "carboxamide compounds" (1) to (5) (1 part), hymexazol (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 66

One of "carboxamide compounds" (1) to (5) (1 part), etridiazole (4 parts), synthesized hydrous silicon oxide (1 part), calcium ligninsulfonate (2 parts), bentonite (30 parts) and kaolin clay (62 parts) are thoroughly mixed and milled. Water is added to the mixture and the mixture is sufficiently kneaded, granulated and then dried to give each of formulations, respectively.

Formulation Example 67

One of "carboxamide compounds" (1) to (5) (12.5 parts), tebuconazole (37.5 parts), calcium ligninsulfonate (3 parts), sodium lauryl sulfate (2 parts) and synthesized hydrous silicon oxide (45 parts) are thoroughly mixed and milled to give each of formulations, respectively.

Formulation Example 68

One of "carboxamide compounds" (1) to (5) (3 parts), prothioconazole (2 parts), kaolin clay (85 parts) and talc (10 parts) are thoroughly mixed and milled to give each of formulations, respectively.

Test Examples using each of the "compositions" are shown in the following.

Test Example 1

A cyclohexanone solution (100 microL) containing prescribed amount (weight) of a test compound was applied on seeds of soybean (variety:Natto shoryu) (10 g) by using a rotary apparatus for seed treatment (Seed dresser, manufactured by Hans-Ulrich Hege GmbH).

One day after the application, plastic pot was filled with soil contaminated by *Rhizoctonia solani*, and the seeds treated with the test compound were seeded in the soil and cultivated in a glass-greenhouse for 20 days (hereinafter referred to as "treated plot").

Thereafter, the presence of disease caused by *Rhizoctonia solani* in the young plants which germinated from each seed was observed and disease severity was calculated according to the following calculation formula (1).

On the other hand, seeds of soybean which were not treated as above were cultivated in the same way as above (hereinafter referred to as "non-treated plot") and disease severity in "non-treated plot" was calculated in the same way as the above "treated plot".

On the basis of the above severities of disease in "treated plot" and "non-treated plot", efficacy in the "treated plot" was evaluated according to the following calculation formula (2).

The results are shown in Table 1 to Table 8.

Disease severity(%)=(number of infected young plants/total number of young plants)×100     Calculation formula (1):

Efficacy (%)=[1−(disease severity in "treated plot"/ disease severity in "non-treated plot")]×100     Calculation formula (2):

TABLE 1

| "carboxamide compound (1)" [g/100 kg of seeds] | triticonazole [g/100 kg of seeds] | efficacy (%) |
|---|---|---|
| 2 | 2 | 100 |

TABLE 2

| "carboxamide compound (5)" [g/100 kg of seeds] | triticonazole [g/100 kg of seeds] | efficacy (%) |
|---|---|---|
| 2 | 2 | 100 |

TABLE 3

| "carboxamide compound (1)" [g/100 kg of seeds] | fFluquinconazole [g/100 kg of seeds] | efficacy (%) |
|---|---|---|
| 2 | 2 | 100 |

TABLE 4

| "carboxamide compound (5)" [g/100 kg of seeds] | fluquinconazole [g/100 kg of seeds] | efficacy (%) |
|---|---|---|
| 2 | 2 | 100 |

TABLE 5

| "carboxamide compound (1)" [g/100 kg of seeds] | ipconazole [g/100 kg of seeds] | efficacy (%) |
|---|---|---|
| 2 | 2 | 100 |

TABLE 6

| "carboxamide compound (5)" [g/100 kg of seeds] | ipconazole [g/100 kg of seeds] | efficacy (%) |
|---|---|---|
| 2 | 2 | 100 |

TABLE 7

| "carboxamide compound (1)" [g/100 kg of seeds] | difenoconazole [g/100 kg of seeds] | efficacy (%) |
|---|---|---|
| 2 | 2 | 100 |

TABLE 8

| "carboxamide compound (5)" [g/100 kg of seeds] | difenoconazole [g/100 kg of seeds] | efficacy (%) |
|---|---|---|
| 2 | 2 | 100 |

Test Example 2

Soil was filled in a plastic pot, and soybean seeds (variety: Nattoshoryu) were seeded in the soil and grown in a greenhouse for 14 days. Test compounds were dissolved in CEC cocktail (cyclohexanone: Solpol™ 2680X (manufactured by Toho Kagaku Kogyo)=5:1 (by volume)) to give an emulsifiable concentrate containing total amount 5% (w/v) of the test compounds. The emulsifiable concentrate was mixed with water to give a prescribed concentration. The mixture was sprayed on leaves of the soybean so as to stick sufficiently thereto. After the spraying, the plant was air-dried, and one day after, the plant was inoculated with an aqueous suspension containing urediniospore of *Phakopsora pachyrhizi* (about 10,000/ml) by spraying the suspension. After the inoculation, the plant was left in humid circumstance at 20-23° C. for one day and then cultivated in a greenhouse for 10 days (hereinafter referred to as "treated plot"). Thereafter, lesion area of *Phakopsora pachyrhizi* was investigated.

On the other hand, soybean was cultivated in the same way as the above "treated plot" except for that the plant was not treated with the mixture containing the test compounds (hereinafter referred to as "non-treated plot"), and the lesion area of *Phakopsora pachyrhizi* were investigated in the same way as above.

On the basis of the above lesion area in "treated plot" and "non-treated plot", effect in the "treated plot" was evaluated according to the following calculation formula (3).

$$\text{Efficacy (\%)}=[1-(\text{lesion area in "treated plot"}/\text{lesion area in "non-treated plot"})]\times 100 \quad \text{Calculation formula (3):}$$

The results are shown in the following Table 9 to Table 22.

TABLE 9

| "carboxamide compound (1)" [ppm] | cyproconazole [ppm] | efficacy (%) |
|---|---|---|
| 2 | 2 | 100 |

TABLE 10

| "carboxamide compound (5)" [ppm] | cyproconazole [ppm] | efficacy (%) |
|---|---|---|
| 2 | 2 | 100 |

TABLE 11

| "carboxamide compound (1)" [ppm] | prothioconazole [ppm] | efficacy (%) |
|---|---|---|
| 2 | 2 | 100 |

TABLE 12

| "carboxamide compound (5)" [ppm] | prothioconazole [ppm] | efficacy (%) |
|---|---|---|
| 2 | 2 | 100 |

TABLE 13

| "carboxamide compound (1)" [ppm] | bromuconazole [ppm] | efficacy (%) |
|---|---|---|
| 2 | 10 | 100 |

TABLE 14

| "carboxamide compound (5)" [ppm] | bromuconazole [ppm] | efficacy (%) |
|---|---|---|
| 2 | 10 | 100 |

TABLE 15

| "carboxamide compound (1)" [ppm] | tebuconazole [ppm] | efficacy (%) |
|---|---|---|
| 2 | 2 | 100 |

TABLE 16

| "carboxamide compound (5)" [ppm] | tebuconazole [ppm] | efficacy (%) |
|---|---|---|
| 2 | 2 | 100 |

TABLE 17

| "carboxamide compound (1)" [ppm] | epoxiconazole [ppm] | efficacy (%) |
|---|---|---|
| 2 | 2 | 100 |

TABLE 18

| "carboxamide compound (5)" [ppm] | epoxiconazole [ppm] | efficacy (%) |
|---|---|---|
| 2 | 2 | 100 |

TABLE 19

| "carboxamide compound (1)" [ppm] | metconazole [ppm] | efficacy (%) |
|---|---|---|
| 2 | 2 | 100 |

TABLE 20

| "carboxamide compound (5)" [ppm] | metconazole [ppm] | efficacy (%) |
|---|---|---|
| 2 | 2 | 100 |

TABLE 21

| "carboxamide compound (1)" [ppm] | tetraconazole [ppm] | efficacy (%) |
|---|---|---|
| 2 | 2 | 100 |

TABLE 22

| "carboxamide compound (5)" [ppm] | tetraconazole [ppm] | efficacy (%) |
|---|---|---|
| 2 | 2 | 100 |

INDUSTRIAL APPLICABILITY

A pesticidal composition comprising a carboxamide compound represented by formula (I) and one or more azole compounds selected from group (A) is useful for controlling pests.

The invention claimed is:

1. A plant disease control composition comprising a carboxamide compound represented by formula (1):

(I)

and one or more azole compounds selected from group (A) consisting of propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, ipconazole, simeconazole, hymexazol, etridiazole and flutriafol, wherein the weight ratio of the carboxamide compound to the azole compound(s) is from 2:1 to 1:4 of the carboxamide compound/the azole compound(s).

2. A method of controlling plant disease which comprises a step of treating a plant or the soil where a plant grows with an effective amount of a carboxamide compound represented by formula (1):

(I)

and one or more azole compounds selected from group (A) consisting of propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, ipconazole, simeconazole, hymexazol, etridiazole and flutriafol, wherein the weight ratio of the carboxamide compound to the azole compound(s) is from 2:1 to 1:4 of the carboxamide compound/the azole compound(s).

3. The method of controlling plant disease according to claim 2, wherein the plant or the soil where a plant grows is soybean or the soil where soybean grows, respectively.

4. A plant disease control composition comprising a carboxamide compound represented by formula (1):

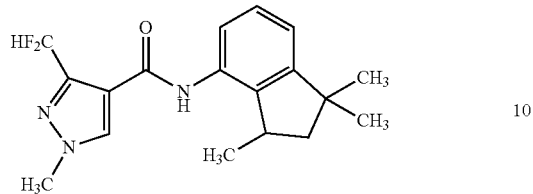
(1)

and tebuconazole,
wherein the weight ratio of the carboxamide compound to tebuconazole is from 2:1 to 1:4 of the carboxamide compound/tebuconazole.

5. A method of controlling plant disease which comprises a step of treating a plant or a soil where the plant grows with an effective amount of the plant disease control composition according to claim 4.

* * * * *